United States Patent
Maerz

(10) Patent No.: US 6,635,223 B2
(45) Date of Patent: Oct. 21, 2003

(54) METHOD FOR INACTIVATING MICRO-ORGANISMS USING HIGH PRESSURE PROCESSING

(76) Inventor: Andreas Maerz, Grossholzstr. 20, Rosenheim (DE)

(*) Notice: Subject to any disclaimer, the term of this patent is extended or adjusted under 35 U.S.C. 154(b) by 0 days.

(21) Appl. No.: 09/845,412

(22) Filed: Apr. 30, 2001

(65) Prior Publication Data

US 2002/0076347 A1 Jun. 20, 2002

Related U.S. Application Data

(63) Continuation-in-part of application No. 09/696,571, filed on Oct. 25, 2000, now abandoned.

(51) Int. Cl.[7] ............................................. A61L 2/00
(52) U.S. Cl. ........................ 422/33; 422/1; 422/3; 422/25; 422/38; 422/39
(58) Field of Search ..................... 422/1, 3, 25, 20, 422/32, 33, 38, 39, 40, 307, 308

(56) References Cited

U.S. PATENT DOCUMENTS

| | | | |
|---|---|---|---|
| 3,619,126 A | * 11/1971 | Carvallo | 422/25 |
| 5,288,462 A | 2/1994 | Carter et al. | 422/39 |
| 5,470,547 A | 11/1995 | Lhenry | 422/295 |
| 5,579,682 A | 12/1996 | Bergman et al. | 99/473 |
| 5,763,028 A | * 6/1998 | Matsumoto et al. | 206/484.2 |
| 5,765,465 A | 6/1998 | Gardin et al. | 92/86 |
| 5,788,934 A | 8/1998 | Lhenry et al. | 422/295 |
| 5,948,356 A | 9/1999 | Lhenry et al. | 422/39 |
| 6,086,936 A | 7/2000 | Wilson et al. | |
| 6,120,732 A | * 9/2000 | Toledo et al. | 422/39 |

FOREIGN PATENT DOCUMENTS

| | | |
|---|---|---|
| EP | 0 588 010 A1 | 7/1993 |
| EP | 0 727 227 A1 | 8/1998 |
| JP | 2089877 | 3/1990 |
| WO | 94/21145 A1 | 9/1994 |
| WO | 94/28745 A1 | 12/1994 |
| WO | 95/21690 A1 | 8/1995 |
| WO | 01/54737 A1 | 8/2001 |
| WO | 02/34074 A1 | 5/2002 |

OTHER PUBLICATIONS

"Pressure Inactivation Of Microorganisms At Moderate Temperatures", P. Butz and H. Ludwig, Physics 139 & 140B, (1986), pp. 875–877.

"Pressure–induced Germination and Inactivation of *Bacillus subtilis* Spores" B. Sojka and H. Ludwig, Pharm. Ind. 56, (1994), pp. 660–663.

(List continued on next page.)

*Primary Examiner*—Krisanne Thornton
(74) *Attorney, Agent, or Firm*—Eugene Stephens & Associates

(57) ABSTRACT

This invention is related to methods for inactivating microorganisms using high pressure processing. A method is described for inactivating micro-organisms in a product using high pressure processing including the steps of packing said product in a flexible container, heating said product to a pre-pressurized temperature, subjecting said product to a pressure at a pressurized temperature for a time period; and reducing the pressure after said time period. The method of the present invention could further comprise an additional step of subjecting said product to a predetermined amount of oxygen for a time interval. The methods of the present invention may be applied preferably to food, cosmetic or pharmaceutical products.

23 Claims, 2 Drawing Sheets

OTHER PUBLICATIONS

"High–pressure Effects in Molecular Biophysics and Enzymology", H. Ludwig, W, Sigalla and B. Sojka, Edited by JL Markley, DB Northrop, and CA Royer, Oxford University Press, New York, Oxford Chapter 22, (1996), pp. 346–363.

"Pressure Effects On Bacteriophage T4", K. Carl and H. Ludwig, High Pressure Research 7, (1991), pp. 176–178.

"Inactivation of microorganisms by hydrostatic pressure", H, Ludwig, C. Bieler, K. Hallbauer, and W, Scigalla, High Pressure and Biotechnology, Colloque INSERM vol. 224, (1992), pp. 25–32.

"Influence of high pressure on a lipid coated virus", P. Butz, G. Habison, and H. Ludwig, High Pressure and Biotechnology, Colloque INSERM vol. 224, (1992), pp. 61–64.

"Pressure Inactivation of Microorganism", H. Ludwig, P. Gross, W. Scigalla, and B. Sojka, High Pressure Research, vol. 12, (1994), pp. 193–197.

"Sterilisation of Radiation and Thermo–Sensitive Pharmaceutical Materials By Means Of High Pressure", W. Scigalla and H, Ludwig, Proceedings of the XXXII Annual Meeting of the European High Pressure Research Group, High Pressure in Material Science and Geoscience, Proc. 32, Technical University, Czech Republic 1994, pp. 195–198.

"Pressure Sensitivity of *Bacillus subtilis* Spores that Survived Previous High Pressure Treatments", B. Sojka and H. Ludwig, Pharm. Iind. 57, Nr.3, 1995, pp. 251–252.

"Pressure Induced Inactivation of Microorganisms", G. VanAlmsick, C. Schreck, and H. Ludwig, Basic and applied high pressure biology IV Jean–Claude Rostain, Alister G, MacDonald and Robert E. Marquid (eds.), Medsubhyp International 1995, tome 5, 1995, pp. 69–75.

"Ultra–high Pressure Decontamination of Insect Biocontrol Preparations", P. Butz, E, Fritsch, J. Huber, B. Keller, H. Ludwig, and B, Tauscher, Biocontrol Science and Technology, 1995, pp. 243–246.

"High pressure inactivation of microorganisms", H. Ludwig, G. vanAlmsick, and B. Sojka, High Pressure Bioscience and Biotechnology, Progress in Biotechnology 13, Ed. By R. Hayashi and C, Balny, Elsevier Science B. V., Amsterdam, The Netherlands, 1996, pp. 237–244.

"Effects of Rapid Pressure Changes on the Inactivation of *Bacillus subtilis* spores," B. Sojka and H, Ludwig, Pharm., Ind. 59. Nr 5, 1997, pp. 436–438.

"Release of Dipicolinic Acid and Amino Acids During High Pressure Treatment of *Bacillus subtilis* Spores", B. Sojka and H. Ludwig, Pharm. Ind. 59 Nr 4, 1997, pp. 355–359.

"Pressure–induced germination of bacterial spores from *Bacillus subtilis* and *Bacillus stearothermophilus*", C. Holters, B. Sojka, and H. Ludwig, High Pressure Research in the Biosciences and Biotechnology, Leuven University Press Ed. By K. Heremans, Leuven University Press, 1997, pp. 257–260.

"The Inactivation of vegetative bacteria by pressure", H. Ludwig and CH Schreck, High Pressure Research in the Biosciences and Biotechnology, Leuven University Press Ed. by K. Heremans, Leuven University Press, 1997, pp. 221–224.

"Influence of UHP on vitamin A acetate content", J. Kubel, H. Ludwig and B. Tauscher, High Pressure Research in the Biosciences and Biotechnology, Leuven University Press Ed. by K. Heremans, Leuven University Press, 1997, pp. 331–334.

* cited by examiner

METHOD FOR INACTIVATING MICRO-ORGANISMS USING HIGH PRESSURE PROCESSING

RELATED APPLICATIONS

This application is a Continuation-In-Part of patent application Ser. No. 09/696,571, filed Oct. 25, 2000 now abandoned, entitled METHOD FOR INACTIVATING MICRO-ORGANISMS USING HIGH PRESSURE PROCESSING, which parent application is hereby incorporated by reference.

BACKGROUND OF THE INVENTION

This invention is related to methods for inactivating micro-organisms using high pressure processing. The methods of the present invention may be applied preferably to food, cosmetic or pharmaceutical products.

Presently, the most conventional and widely used technique for inactivating micro-organisms and for sterilising products is thermal processing. Thermal sterilisation methods, such as the autoclaving of canned foods, are commonly used to extend the shelf life of food products. In the medical field, thermal processing is employed in sterilising, for example, various medical instruments. Although conventional thermal sterilisation methods are quite effective for inactivating a wide range of both vegetative and non-vegetative forms of micro-organisms on many types of products, there are several disadvantages. For example, thermal sterilisation often affects the natural taste, colour and/or texture of many products. Further, there are products which cannot be sterilised using conventional thermal processing because the structure would be destroyed. Thus, there is a need for effective alternative methods for inactivating micro-organisms that involve limited heat treatment and moreover do not affect many of the desired substances in products.

As an alternative to conventional thermal sterilisation techniques, the effectiveness of high pressure processing at ambient temperatures for inactivating micro-organisms in food has been known since the early 1900s. Although the inactivation of micro-organisms at high pressures is not completely understood, it is generally believed that micro-organisms are destroyed through altered permeability of the cell membranes from mechanical disruptions or through protein denaturation due to the disruption of hydrophobic and ionic bonds, and subsequent unfolding of the protein source. High pressure processing has demonstrated several advantages over conventional thermal sterilisation methods. Heat treatment of the product can be avoided or limited. The natural taste, colour and texture of many products are preserved, as well as the nutritional value and vitamin content. Further, chlorophyll and most aroma substances remain intact after high pressure processing. Physical damage to the food is also less using high pressure processing.

Japan introduced the first commercial food products to be sterilised using high pressure processing in 1990. Since then the high pressure sterilisation of foods has become widely accepted, and presently, there are several high pressure processed products on the market, including fruit, yoghurt, jam, jellies and fruit sauces.

Commercialised high pressure processing methods in the food industry generally involve placing food packed in a container inside a pressure vessel which contains a pressure transmitting medium (e.g. water). After the vessel is closed, the pressure is raised to a desired level by pumping the transmitting medium into the vessel by means of an external pressure intensifier. The vessel temperature can be maintained usually between +10 and +70° C. The pressure is kept for a required time period. Then, the pressure is decreased. High pressure processing methods tend to vary depending on the settings for the pressure, temperature, time period and transmitting medium. Since the temperature of the vessel may be set, high pressure processing may also involve a combined application of elevated temperatures and high pressures.

In general, it has been found that pressure levels of approx. 600 MPa at 25° C. are sufficient to totally inactivate vegetative forms of micro-organisms. Low pressure (400–600 MPa) applied for a restricted time period (5–10 min at 25° C.) has proved effective in the destruction of common contaminating micro-organisms in food. In the case of pathogenic vegetative forms of micro-organisms, total inactivation required slightly higher levels of processing (500–600 MPa). To destroy yeast and mould, lower levels of pressure/time period were sufficient at 25° C. Thus, high pressure processing at ambient temperatures has been proven to be very effective for inactivating non-spore forming pathogens, vegetative bacteria, yeast and moulds.

However, the effects of high pressures at ambient temperatures on the destruction of non-vegetative forms of micro-organisms, e.g. bacterial spores, has proven to be limited. Some research in the field indicates that the inactivation of such micro-organisms is possible using a combination of high pressures and elevated temperatures. For example, the inactivation of clostridia spores, bacilli and heat resistant moulds in technologically short time periods proved to be possible with processing at 900 MPa and simultaneously conditioning between 50 and 80° C.

U.S. Pat. No. 6,086,936 describes a method for sterilising foods using both ultra-high pressures and high temperatures. The method involves heating a food to a pre-pressurised temperature, subjecting the food to ultra-high pressure, which instantaneously raises the temperature of the food, and then releasing the pressure so that the temperature returns to the original pre-pressurised temperature. The method leverages the adiabatic temperature rise which occurs when the food is hydrostatically pressurised, coupled with the lethality of the pressure, to achieve appropriate sterilisation conditions. The method disclosed however seems to be restricted to food, in particular non-dairy food products having a pH equal to or greater than 4.6.

In the cosmetic and pharmaceutical industries, there is a need for effective sterilisation techniques which do not reduce or alter the potency of the active substances in the product. Due to the high temperatures employed, it is not possible to use conventional heat sterilisation methods on many temperature-sensitive pharmaceutical products without negatively affecting the efficacy of the active substance. Therefore, a more gentle and equally effective means for sterilising such products would represent a significant technical advantage in the field. The potential to process cosmetic and pharmaceutical products using high pressure processing is already recognised as a viable option to current methods. However, an optimal method for inactivating micro-organisms in cosmetic and pharmaceutical products has not been disclosed by the prior art.

In "Pressure inactivation of micro-organisms at moderate temperatures" (Butz, P and Ludwig, H; Physica 139&140 B, 1986), "High Pressure inactivation of bacteria and bacteria spores" (Butz, P, Ludwig, H et al; Pharm. Ind. 52, 1990), "Pressure induced germination and inactivation of *Bacillus subtillis* spores" (Sojka, B and Ludwig, H; Pharm. Ind. 56, 1994) and "Pressure and temperature induced inactivation of micro-organisms" (Ludwig, H, Scigalla,W and Sojka, B; High Pressure Effects in Molecular Biophysics and Enzymology-Northrop and Royer, Chapter 22, 1996), methods using a combination of high pressures and elevated temperatures are discussed for inactivating micro-organisms, primarily bacteria and bacterial spores, with applications to the drug industry. Various parameters are investigated in order to ascertain the optimal conditions for destroying the micro-organisms mentioned. For example, in the article from Sojka and Ludwig in Pharm. Ind of 1994, the pressure inactivation of bacterial spores was studied in the range from 600 to 6000 bar at temperatures of 40 and 50° C. At 40° C., the number of germs could be reduced by a factor of $10^6$ after 210 min. of pre-treatment at 600 bar and following inactivation at 5000 bar for some minutes. Raising the temperature to 50° C., an alternating pressurisation at 600 and 5000 bar in intervals of 30 min. led to the complete inactivation of spores after an overall time of 180 min. In the aforementioned "Pressure and temperature induced inactivation of micro-organisms" of 1996, results showed that pressure cycles are useful for the inactivating spores and further that the addition of ethanol promotes inactivation.

In the aforementioned references, several options are considered for yielding a method for destroying specific bacteria and bacterial spores whilst at the same time minimising the parameters of temperature, pressure and duration of the pressure applied. However, optimal parameters for a method of inactivating a wide range of micro-organisms, including non-vegetative forms, using high pressure processing that may also be safely applied to pharmaceutical products is yet to be determined.

OBJECT OF THE INVENTION

It is therefore an object of the present invention to provide a more effective method for inactivating micro-organisms using high pressure processing.

The object of the present invention is achieved with the features of the claims.

SUMMARY OF THE INVENTION

The subject-matter according to the present invention has the particular advantage that it can be safely applied to pharmaceutical and cosmetic products without affecting the efficacy of the active substances in the products.

Another advantage of the present invention exists in providing an innovative method for inactivating micro-organisms using high pressure processing that is effective for inactivating even difficult-to-destroy non-vegetative bacteria and bacterial spores and at the same time, requires lower temperatures, lower pressures and shorter pressure application time periods as that of known methods.

The present invention provides an improved method for inactivating micro-organisms using high pressure processing. A combination of high pressures and elevated temperatures are used to inactivate even worst case bacterial spores. Although heat is applied to the product, the heat applied is generally significantly lower than that of conventional thermal sterilisation processes. Thus, the present method would still be considered as more desirable than conventional thermal processes for heat-sensitive products.

Further, the methods of the present invention introduce new factors which can be used to minimise the high pressure processing parameters necessary for inactivating specific micro-organisms, such as the required temperature and pressure applied to the product. It has been found that the effects of high pressure processing on the inactivation of micro-organisms may be greatly enhanced by pre-treating the product with specified amounts of oxygen. Since oxygen pre-treatment can promote inactivation, the processing parameters required in order to achieve the same micro-organism reduction criteria can be somewhat lower than the parameters required in methods without pre-treatment. In other words, lower processing temperatures and pressures at shorter time periods can be employed.

It was recognised surprisingly by experimentation that, when using products packed in flexible containers, oxygen pathways resulting from the high pressures of the transmitting medium applied appear to influence the amount of micro-organisms reduced. The presence of oxygen pathways contributed to increasing the overall effectiveness of the inactivation process. Thus, it is believed that by pre-treating the product using specified amounts of oxygen, one can further increase the effectiveness of the high pressure processing methods thereby simultaneously allowing a reduction of the processing parameters.

It is well known that oxygen is highly toxic because oxidation reactions can inactivate enzymes. An improved method which incorporates this factor can provide a very effective way to inactivate micro-organisms requiring minimised processing parameters, i.e. lower temperatures and pressures at shorter time intervals as that of known methods. Methods requiring minimised processing parameters are more desirable when processing sensitive products such as pharmaceuticals.

Another surprising factor is the influence of the various types of packaging on the high pressure processing methods. Several containers were tested and not all conventional containers were proven to be suitable under particular processing conditions. Thus, a consideration of the appropriate packaging has to be made in order to assure minimal damage to the product.

DETAILED DESCRIPTION OF THE INVENTION

One preferred embodiment of the present invention is a method for inactivating micro-organisms using high pressure processing comprising the steps of; a) heating a product to a pre-pressurised temperature, b) placing the product in a pressure vessel, c) subjecting the product to a pressure at a pressurised temperature for a time period in the presence of a transmitting pressure fluid, d) reducing the pressure in the vessel after said time period, e) removing the product from said pressure vessel, wherein said method steps c) and d) may be repeated at least once before step e) is performed, said time period and said pressure being adjustable between repetitions of steps c) and d).

The aforementioned embodiment may further comprise an additional step before step b) of subjecting the product to an predetermined amount of oxygen for a time interval.

The product is heated to a pre-pressurised temperature using preferably a water bath. The pre-pressured temperature is preferably greater than ambient temperature and less than 70° C. The transmitting pressure fluid in the pressure vessel is preferably water.

The pressure in the pressure vessel is preferably between 500 and 8000 bar, and preferably able to be incrementally increased and decreased. The pressurised temperature is preferably between 20 and 100° C.

During the high pressure process, the pressure has a uniform effect on the entire pre-packaged product. The flexibility of the product's container enables it to compensate for external pressure through a reduction in volume. Thus, flexible containers are preferable.

Another preferred embodiment of the present invention is a method for inactivating micro-organisms using high pressure processing comprising the steps of; a) subjecting a product to a pre-determined amount of oxygen for a time interval, b) placing the product in a pressure vessel, c) subjecting the product to a pressure at a pressurised temperature for a time period in the presence of a transmitting pressure fluid, d) reducing the pressure in the vessel after said time period, e) removing the product from said pressure vessel, wherein said method steps c) and d) may be repeated at least once before step e) is performed, said time period and said pressure being adjustable between repetitions of steps c) and d).

The pressure in the pressure vessel is preferably between 500 and 8000 bar, and preferably able to be incrementally increased and decreased. The pressurised temperature is preferably between 20 and 100° C. The transmitting pressure fluid in the pressure vessel is preferably water. The product is preferably pre-packed in a flexible container.

The present invention can be utilised to process a variety of products, especially food, cosmetic and pharmaceutical products.

BRIEF DESCRIPTION OF THE DRAWINGS

Using the following figures, preferred embodiments of the invention are described in further detail.

DESCRIPTION OF THE PREFERRED EMBODIMENTS

Figure 1:
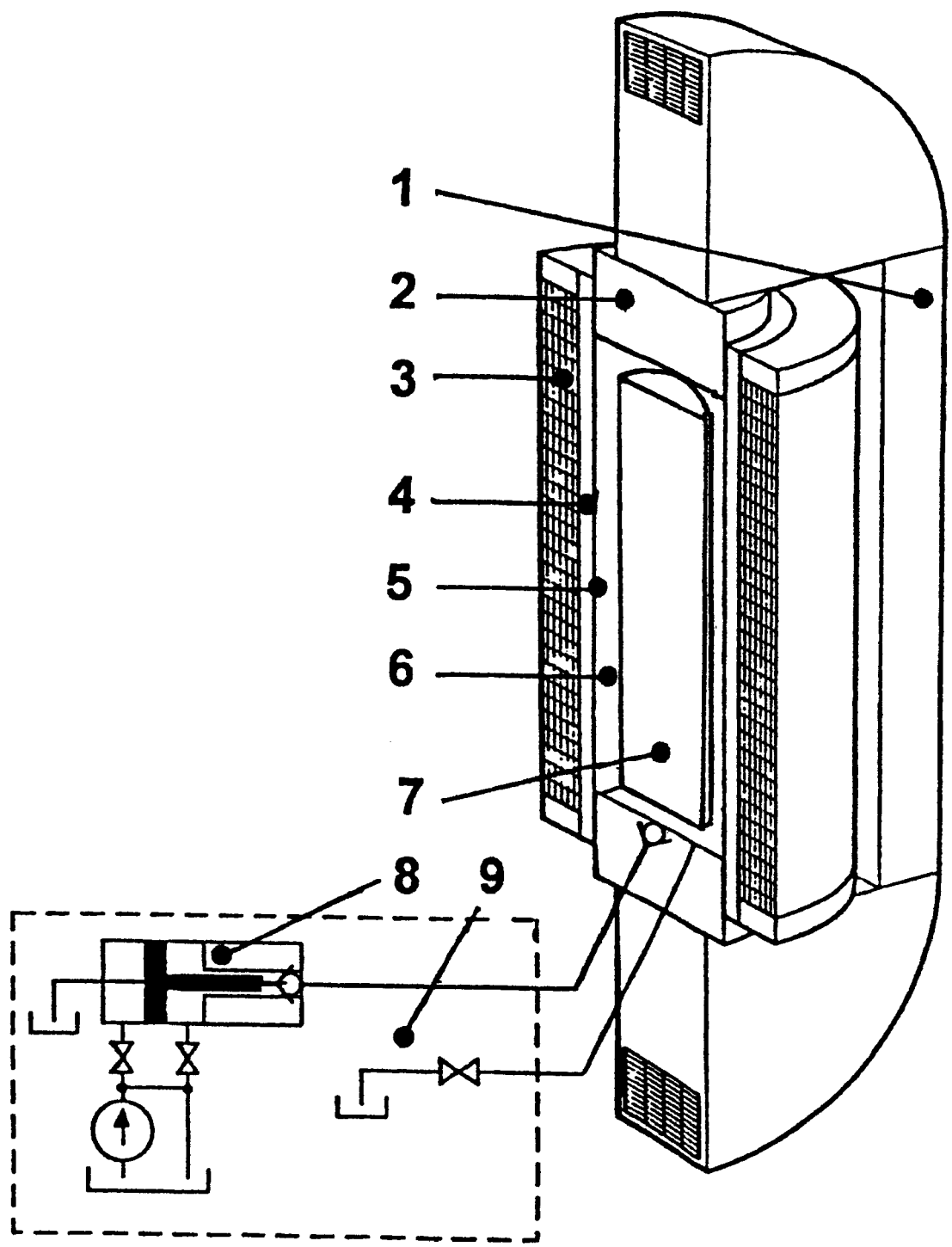
FIG. 1: shows a conventional high pressure processing device
Figure 2:
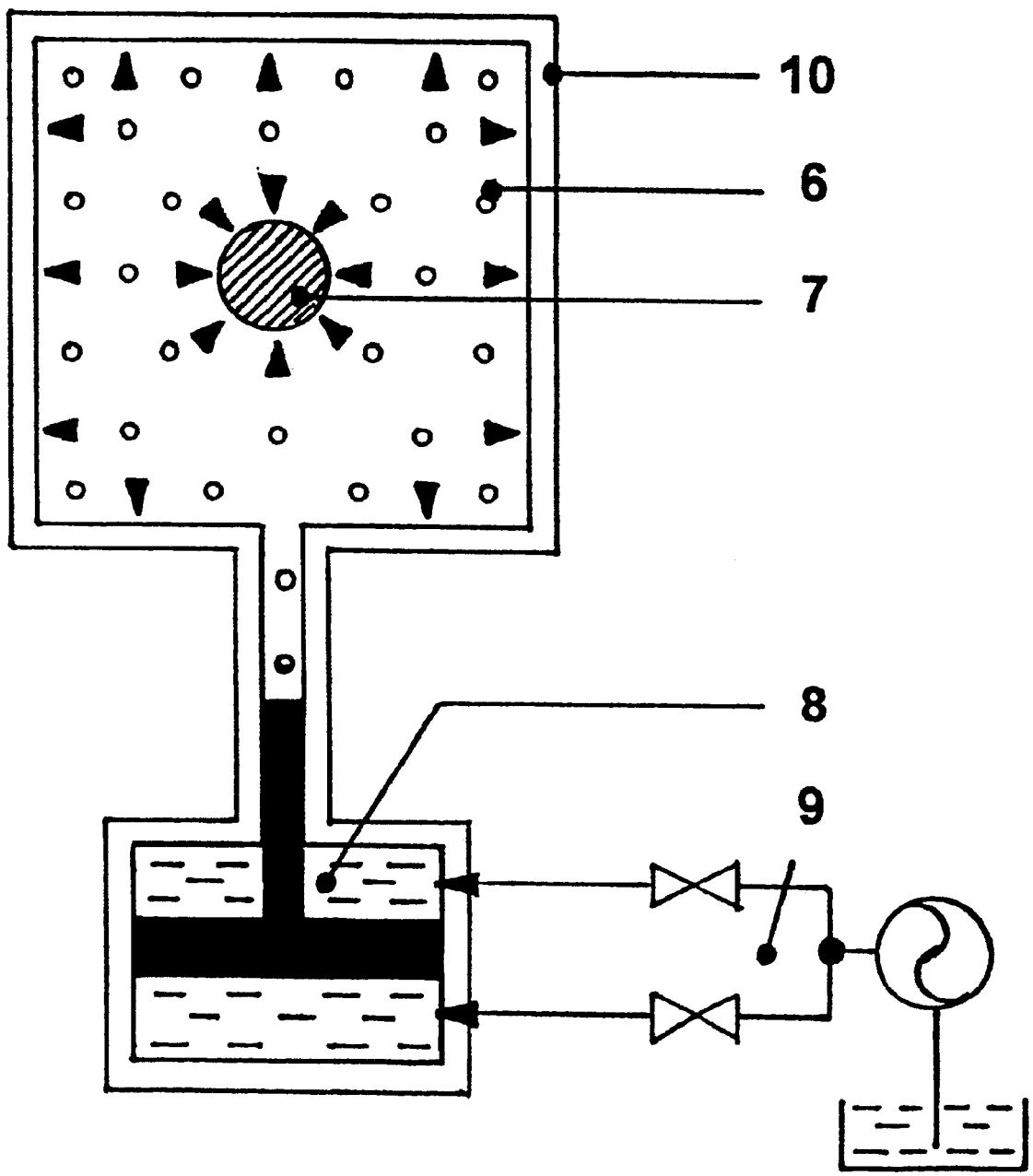
FIG. 2: illustrates a pressure vessel used in a conventional high pressure processing device

In the first embodiment of the present invention, a pre-packaged product 7 is initially heated in preferably a water bath until a pre-pressurised temperature is reached. This temperature is preferably between 30 and 70° C. Referring to FIGS. 1 and 2, the pre-packaged product 7 is then placed into a pressure vessel 10 located within a pressure cylinder 4. The pressure vessel 10 contains a pressure transmitting medium 6, preferably water. After the pressure vessel 10 is closed, the pressure is raised to a desired level by pumping the transmitting medium 6 into the pressure vessel 10 by means of an external pressure intensifier 8. Once the desired pressures and temperatures are achieved in the pressure vessel 10, they are maintained for a pre-determined time period. After the time period has expired, the pressure and temperature are reduced. The pre-packaged product is then removed from the pressure vessel 10.

The pre-packed product can also be processed using intervals having different or the same processing parameters. For example, after the first high pressure process (i.e. previously mentioned steps c) and d)), the product can be processed again before it is removed from the pressure vessel 10 by resetting the parameters. To allow this, the pressure in the pressure vessel 10 may be increased or decreased. Once the newly set pressure is achieved in the pressure vessel 10, it is maintained for the newly set time period.

In order to inactivate a wide range of micro-organisms using the methods of the present invention, several processing parameters were experimentally tested in order to determine effective and robust methods.

For the protection of the consumer, pharmaceutical preparations must meet several microbiological purity criteria. The criteria for the various pharmaceutical products differ depending on the category to which they belong. Products that have a greater potential for harming the consumer are placed in categories having stricter criteria.

In order to meet such criteria, a wide range of micro-organisms were experimentally tested ranging from vegetative bacteria to bacterial spores. The tested bacteria included *Staphylococcus auras* (STA), *Escherichia coli* (EC), *Pseudomonas aeruginosa* (PSA), *Candida albicans* (CA), *Clostridium sporogenes* (CL), *Bacillus subtillus* (BS) and *Aspergillus niger* (AN).

Firstly, concentrations of the bacteria were made by culturing according to standard techniques. The samples were prepared by mixing the bacteria with a salt solution in order to obtain a concentration of $10^6$ KBE/ml. The following 5 samples were tested:

A: a mixed suspension of EC and PSA

B: a mixed suspension of STA and BS

C: a mixed suspension of CA and AN

D: CL(1)

E: CL(2)

Two samples of clostridium sporogenes were prepared, so that the processing parameters necessary for inactivating these spores could be tested for robustness. These spores were considered as difficult-to-destroy and thus termed the worst case bacteria.

Each of the samples were filled into five different types of containers, so that the feasibility of using the various conventional containers could also be tested. Each sample was filled into 1) a 20 ml PE screwable bottle, 2) a 30 ml PE tube, 3) a 10 ml PE-AT vial, 4) a 20 ml PE-ampoule and 5) a 20 ml flexible film container.

The test results of two different processing parameters are shown in Tables 1 and 2. Tables 1 and 2 illustrate the reduction factors in $\log_{10}$ for each of the tested micro-organisms after the samples were processed.

Referring to Table 1, the pre-packaged sample was first heated in a water bath until a pre-pressured temperature of 32° C. was achieved. The sample was then placed in a pressure vessel 10. The pressure in the pressure vessel 10 was brought to 6000 bar, and the sample was pressurised at a temperature of 60° C. After a time period of 300 min, the pressure was reduced.

A reduction factor greater than $10^6$ (>6) was considered adequate for reaching acceptable micro-organism inactivation conditions. As seen in Table 1, these parameters were not adequate for inactivating clostridium sporegenes in all containers tested and bacillus subtillus in the flexible film containers. However, bacillus subtillus was suitably reduced in other containers. Further, the other tested bacteria was suitably reduced in all containers.

TABLE 1

Reduction factors in log$_{10}$: parameters (300 min, 6000 bar, 60° C.)

| Samples | RF$_{EC60}$ | RF$_{PSA60}$ | RF$_{STA60}$ | RF$_{BS60}$ | RF$_{CA60}$ | RF$_{AN60}$ | RF$_{CL60(1)}$ | RF$_{CL60(2)}$ |
|---|---|---|---|---|---|---|---|---|
| 20 ml-PE-Screwable Bottle | >6 | >6 | >6 | >6 | >6 | >6 | 0 | 1 |
| 30 ml-PE-Tube | >6 | >6 | >6 | >6 | >6 | >6 | 1 | 1 |
| 10 ml-PE-AT-Vial | >6 | >6 | >6 | >6 | >6 | >6 | 1 | 1–2 |
| 20 ml-PE-Ampoule | >6 | >6 | >6 | >6 | >6 | >6 | 1–2 | 2 |
| 20 ml-film container | >6 | >6 | >6 | 5 | >6 | >6 | 1 | 1–2 |

TABLE 2

Reduction factors in log$_{10}$: parameters (180 min, 6000 bar, 90° C.)

| Samples | RF$_{EC90}$ | RF$_{PSA90}$ | RF$_{STA90}$ | RF$_{BS90}$ | RF$_{CA90}$ | RF$_{AN90}$ | RF$_{CL90(1)}$ | RF$_{CL90(2)}$ |
|---|---|---|---|---|---|---|---|---|
| 20 ml-PE-Screwable Bottle | >6 | >6 | >6 | >6 | >6 | >6 | >6 | >6 |
| 30 ml-PE-Tube | >6 | >6 | >6 | >6 | >6 | >6 | >6 | >6 |
| 10 ml-PE-AT-Vial | >6 | >6 | >6 | >6 | >6 | >6 | >6 | >6 |
| 20 ml-PE-Ampoule | >6 | >6 | >6 | >6 | >6 | >6 | >6 | >6 |
| 20 ml-film container | >6 | >6 | >6 | 5 | >6 | >6 | 4 | 4 |

Referring to Table 2, the pre-packaged sample was first heated in a water bath until a pre-pressured temperature of 50° C. was achieved. The sample was then placed in a pressure vessel 10. The pressure in the pressure vessel 10 was brought to 6000 bar and the sample was pressurised at a temperature of 60° C. After a time period of 180 min, the pressure was reduced.

As seen in Table 2, these parameters prove to be effective for inactivating all the micro-organisms tested. However, clostridium sporegenes in the flexible film containers were still not sufficiently inactivated. Experimental results indicate that the use of certain laminated flexible film containers under such processing conditions may hinder the effectiveness of the method and thus the containers do not play an insignificant role in the inactivation of micro-organisms using high pressure processing.

The various embodiments and experimental results presented in the specification are used for the sake of description and clarification of the invention, and thus should not be interpreted as limiting the scope of the invention as such. The invention is represented by the claims and any obvious modifications thereof.

What is claimed:

1. A method for inactivating micro-organisms in a product using high pressure processing comprising the steps of:
   a) packing said product in a flexible container;
   b) heating said product to a pre-pressurised temperature;
   c) subjecting said product to a pressure of at least 500 bar at a pressurised temperature for a time period, the pressure being applied to the product through the flexible container, wherein a volume of the flexible container is subject to reduction in response to the applied pressure; and
   d) reducing the pressure after said time period.

2. The method of claim 1 further comprising an additional step before step b) of subjecting said product to a predetermined amount of oxygen for a time interval.

3. The method of claim 1, wherein said product is heated to the pre-pressurised temperature in a water bath.

4. The method of claim 1, wherein the pre-pressured temperature is preferably greater than 25° C. and less than 70° C.

5. The method of claim 1, wherein method steps c) and d) are repeated at least once and said time period and said pressure being adjustable between repetitions of steps c) and d).

6. The method of claim 1, wherein between method steps b) and c) said product is placed in a pressure vessel and removed therefrom after step d).

7. The method of claim 1, wherein the pressure is transmitted using a pressure fluid.

8. The method of claim 1, wherein the pressure is between 500 and 8000 bar.

9. The method of claim 1, wherein the pressure is incrementally increased or decreased.

10. The method of claim 1, wherein the pressurised temperature is between 20 and 100° C.

11. The method of claim 1, wherein the flexible container is a PE ampoule.

12. A method for inactivating micro-organisms in a product using high pressure processing comprising the steps of:
   a) packing said product in a flexible container;
   b) subjecting said product to a pre-determined amount of oxygen for a time interval, said pre-determined amount of oxygen being sufficient to induce oxidation reactions toxic to aerobic as well as anaeorobic microorganisms;
   c) subjecting said product to a pressure of at least 500 bar at a pressurised temperature for a time period, the pressure being applied to the product through the flexible container, wherein a volume of the flexible container is subject to reduction in response to the applied pressure; and
   d) reducing the pressure after said time period.

13. The method of claim 12, wherein method steps c) and d) are repeated at least once and said time period and said pressure being adjustable between repetitions of steps c) and d).

14. The method of claim 12, wherein between method steps b) and c) said product is placed in a pressure vessel and removed therefrom after step d).

15. The method of claim 12, wherein pressure is transmitted using a pressure fluid.

16. The method of claim 12, wherein the pressure is between 500 and 8000 bar.

17. The method of claim 12, wherein the pressure is incrementally increased or decreased.

18. The method of claim 12, wherein the pressurised temperature is between 20 and 100 ° C.

19. The method of claim 12, wherein the flexible container is a PE ampoule.

20. The method of claim 1 wherein said product is a pharmaceutical product.

21. The method of claim 1 wherein said product is a cosmetic product.

22. The method of claim 12 wherein said product is a pharmaceutical product.

23. The method of claim 12 wherein said product is a cosmetic product.

* * * * *